United States Patent [19]

McCall

[11] Patent Number: 4,711,960

[45] Date of Patent: Dec. 8, 1987

[54] ISOCHROMANS

[75] Inventor: John M. McCall, Kalamazoo, Mich.

[73] Assignee: The Upjohn Company, Kalamazoo, Mich.

[21] Appl. No.: 823,343

[22] Filed: Jan. 28, 1986

Related U.S. Application Data

[60] Division of Ser. No. 718,199, Apr. 1, 1983, Pat. No. 4,577,021, which is a continuation of Ser. No. 26,719, Apr. 4, 1979, abandoned, which is a continuation-in-part of Ser. No. 847,350, Oct. 31, 1977, abandoned.

[51] Int. Cl.$^4$ ............................................ C07D 405/04
[52] U.S. Cl. ..................................... 544/364; 544/376; 546/194; 546/196; 546/199

[58] Field of Search ................ 544/376, 364; 546/194, 546/196, 199

[56] References Cited

U.S. PATENT DOCUMENTS 3,467,675 9/1969 Petersen et al. .................... 544/376
4,006,648 1/1973 Yoshikaza Oka et al. ......... 544/376

Primary Examiner—Glennon H. Hollrah
Assistant Examiner—James H. Turnipseed
Attorney, Agent, or Firm—Sidney B. Williams, Jr.

[57] ABSTRACT

Isochromans, isothiochromans, 2-benzoxepins and 2-benzothiepins are described. The compounds possess hypotensive and anti-psychotic properties; methods and compositions using them are described.

2 Claims, No Drawings

ISOCHROMANS

CROSS-REFERENCE TO RELATED APPLICATION

This application is a division of copending application Ser. No. 718,199, filed Apr. 1, 1983, now U.S. Pat. No. 4,577,021 which is a continuation of Ser. No. 026,719 filed Apr. 4, 1979, now abandoned which in turn is a continuation-in-part of copending application Ser. No. 847,350, filed Oct. 31, 1977, now abandoned.

SUMMARY OF THE INVENTION

The present application relates to novel compounds which are amines of certain isochromans. In particular the present invention relates to the novel isochromans disclosed in U.S. Ser. No. 858,303, filed Dec. 7, 1979, now issued as a U.S. Pat. No. 4,153,612, the disclosure of which is incorporated here by reference.

In particular, now U.S. Pat. No. 4,153,612, describes the use of certain isochromans as intermediates for preparing isochroman amine type compounds. With respect to the specification of U.S. Pat. No. 4,153,612, particular reference is made to Tables 14 and 15 therein.

Moreover, the examples 20, 21a, 21b and 21c provide examples of preparation of amines according to formulas of Tables 14 and 15 therein. Accordingly, there are described:

4-(4-chlorophenyl)-1-[(3,4-dihydro-6,7-dimethoxy-4,4-dimethyl-1H-2-benzopyran-1-yl)methyl]-1,2,3,6-tetrahydro-pyridine, monohydrochloride in Example 20;

1-[3-(3,4-dihydro-6,7-dimethoxy-1-methyl-1H-2-benzopyran-1-yl)propyl]-4,(4-fluorophenyl)-piperazine, dihydrochloride in Example 21a;

1-[2-(6,7-dimethoxy-4,4-dimethylisochroman-1-yl)ethyl]-4-(3-trifluoromethylphenyl)piperazine, dihydrochloride in Example 21b; and 2-[-[(6,7-dimethoxy-4,4-dimethylisochroman-1-yl)-ethyl]-6,7-dimethoxy-1,2,3,4-tetrahydroisoquinoline monohydrochloride in Example 21c.

As indicated in the text associated with Table 14 in U.S. Pat. No. 4,153,612, the method of preparing the isochroman amine type compounds of Table 14 in the manner of Examples 20, 21a and 21b from the appropriate (6,7-dimethoxy-isochroman-1-yl)alkyl halides and the appropriate amines. Likewise, certain additional isochroman amine type compounds represent novel chemical entities comprising one aspect of the present invention. Moreover, these novel compounds are prepared by following procedures similar to those of Examples 20, 21a and 21b in U.S. Pat. No. 4,153,612, but substituting the appropriate (6,7-dimethoxyisochroman-1-yl)alkyl halides and the appropriate amines. (Table I).

Compounds of Tables I and II above are within the preferred compounds of U.S. Pat. No. 4,153,612, Formula I'. Compounds within this group having an alkyl group of one through three carbons at one of the positions $R_2$ through $R_5$ or $R_8$ are more preferred. Further, new compounds of this invention, i.e., 4-(2-chlorophenyl)-1-[2-(3,4-dihydro-6,7-dimethoxy-4,4-dimethyl-5H-2-benzopyran-1-yl)ethyl]piperazine and 4-(3-chlorophenyl-1-[2-3,4-dihydro-6,7-dimethoxy-4,4-dimethyl-1H-benzopyran-1-yl)ethyl]piperazine are among those specifically preferred compounds of Formula I' as described in now U.S. Pat. No. 4,153,612. In addition compounds prepared herein having alkyls of from one to three atoms, inclusive, at the $R_4$ and $R_5$ positions of Formula I', wherein b is zero and $R_8$ is hydrogen are now also found to be among those specifically preferred in the present invention.

Further, the present invention now comprises the unexpected discovery that certain of the isochroman amine type compounds of U.S. Pat. No. 4,153,612, and Tables I and II of this disclosure exhibit a split in activity between an anti-psychotic and a hypotensive effect. In other words, such compounds have either first, a high anti-psychotic and low cardiovascular effect or second, a low anti-psychotic and high cardiovascular effect. The effect of the first split recited above is exhibited by 4-phenyl-1-[2-(3,4-dihydro-6,7-dimethoxy-4,4-dimethyl-1H-2-benzopyran-1-yl)ethyl]-1,2,3,6-tetrahydropyridine monohydrochloride hemihydrate, listed as the eighth compound in Table 14 of U.S. Pat. No. 4,153,612, 4-phenyl-1-[2-(3,4-dihydro-6,7-dimethoxy-4-methyl-1H-2-benzopyran-1-yl)ethyl]-1,2,3,6-tetrahydropyridine and 4-(2-chlorophenyl)-1-[2-(3,4-dihydro-6,7-dimethoxy-4-methyl-1H-2-benzopyran-1-yl)ethyl]-piperazine, the latter compounds are included in Table I herein. The effect of the second split recited above is exhibited by 4-phenyl-1-[3-(3,4-dihydro-6,7-dimethoxy-1-methyl-1H-2-benzopyran-1-yl)pyran]-1,2,3,6-tetrahydropyridine, 4-phenyl-1-[3-(3,4-dihydro-6,7-dimethoxy-1,4,4-trimethyl-1H-2-benzopyran-1-yl)propyl]-1,2,3,6-tetrahydropyridine, 4-phenyl-1-[3-[1-(4-fluorophenyl)-3,4-dihydro-6,7-dimethoxy-4,4-dimethyl-1H-2-benzopyran-1-yl]propyl-1,2,3,6-tetrahydropyridine and 4-phenyl-1-[3-(3,4-dihydro-6,7-dimethoxy-1,4-dimethyl-1H-2-benzopyran-1-yl)propyl]-1,2,3,6-tetrahydropyridine, all shown in Table I above.

In the formulation of compounds in the present invention for pharmacological utility conventional techniques are used as fully disclosed in U.S. Pat. No. 4,153,612.

TABLE I

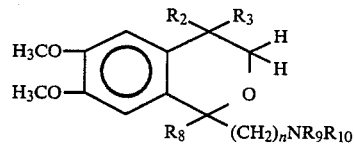

| HNR9R10 | n | R2 | R3 | R8 | °C./Hrs. Misc. | M.P. (°C.) | Anal. (Found) | Name |
|---|---|---|---|---|---|---|---|---|
| H—N⟨piperidine⟩⟨phenyl⟩ | 3 | H | H | CH3 | | 197–199<sup>a</sup> | | 4-phenyl-1-[3-(3,4-dihydro-6,7-dimethoxy-1-methyl-1H—2-benzopyran-1-yl)propyl]-1,2,3,6-tetrahydropyridine. |

TABLE I-continued $$\text{Structure: } H_3CO\text{-, }H_3CO\text{- substituted benzopyran with } R_2, R_3, R_8, \text{ and }(CH_2)_n NR_9R_{10}$$

| HNR₉R₁₀ | n | R₂ | R₃ | R₈ | °C./Hrs. Misc. | M.P. (°C.) | Anal. (Found) | Name |
|---|---|---|---|---|---|---|---|---|
| H—N(piperazine)N-(2-chlorophenyl) | 2 | H | CH₃ | H | | 170–172$^d$ decomposes | | 4-(2-chlorophenyl)-1-[2-(3,4-dihydro-6,7-dimethoxy-4-methyl-1H—2-benzopyran-1-yl)ethyl]piperazine. |
| H—N(piperazine)N-(2-pyridyl) | 3 | H | H | CH₃ | | 230–231° C. | as mono MeOH.HCl C, 58.31; H, 7.10; N, 8.14; Cl, 13.75 | 4-(2-pyridyl)-1-[3-(3,4-dihydro-1-methyl-6,7-dimethoxy-1H—2-benzopyran-1-yl)propyl]piperazine. |
| H—N(piperazine)N-phenyl | 2 | CH₃ | H | H | | 190–191$^d$ | C, 50.95; H, 7.32; N, 6.22; Cl, 14.86 | 4-phenyl-1-[2-(3,4-dihydro-6,7-dimethoxy-4-methyl-1H—2-benzopyran-1-yl)ethyl]piperazine. |
| H—N(tetrahydropyridine)-phenyl | 2 | CH₃ | H | H | | 202–204$^a$ | C, 69.49; H, 7.63; N, 2.98; Cl, 8.35 | 4-phenyl-1-[2-(3,4-dihydro-6,7-dimethoxy-4-methyl-1H—2-benzopyran-1-yl)ethyl]-1,2,3,6-tetrahydropyridine. |
| H—N(piperazine)N-phenyl | 3 | CH₃ | CH₃ | CH₃ | | 225–227$^d$ | C, 63.79; H, 7.93; N, 5.53; Cl, 13.01 | 4-phenyl-1-[3-(3,4-dihydro-6,7-dimethoxy-1,4,4-trimethyl-1H—2-benzopyran-1-yl)propyl]piperazine. |
| H—N(tetrahydropyridine)-phenyl | 3 | CH₃ | CH₃ | CH₃ | | 221–223$^b$ | C, 70.43; H, 7.80; N, 2.93; Cl, 7.70 | 4-phenyl-1-[3-(3,4-dihydro-6,7-dimethoxy-1,4,4-trimethyl-1H—2-benzopyran-1-yl)propyl]-1,2,3,6-tetrahydropyridine. |
| H—N(piperazine)N-(2-methylphenyl) | 3 | CH₃ | CH₃ | CH₃ | | 223–225$^a$ | C, 68.44; H, 8.28; N, 5.47; Cl, 7.02 | 4-(2-methylphenyl)-1-[3-(3,4-dihydro-6,7-dimethoxy-1,4,4-trimethyl-1H—2-benzopyran-1-yl)propyl]piperazine. |
| H—N(tetrahydropyridine)-phenyl | 3 | CH₃ | CH₃ | 4-fluorophenyl | | 112–115$^c$ | C, 69.21; H, 7.36; N, 2.48; Cl, 6.66 | 4-phenyl-1-[3-[1-(4-fluorophenyl)-3,4-dihydro-6,7-dimethoxy-4,4-dimethyl-1H—2-benzopyran-1-yl]propyl]-1,2,3,6-tetrahydropyridine. |
| H—N(piperazine)N-(4-fluorophenyl) | 3 | CH₃ | CH₃ | CH₃ | | 231–233$^g$ | C, 60.72; H, 7.30; N, 5.14; Cl, 12.91; F, 5.24 | 4-(4-fluorophenyl)-1-[3-(3,4-dihydro-6,7-dimethoxy-1,4,4-trimethyl-1H—2-benzopyran-1-yl)propyl]piperazine. |
| H—N(piperazine)N-phenyl | 3 | CH₃ | CH₃ | 4-fluorophenyl | | 225–227$^c$ | C, 66.86; H, 7.21; N, 4.97; Cl, 7.17; F, 3.22 | 4-phenyl-1-[3-[1-(4-fluorophenyl)-3,4-dihydro-6,7-dimethoxy-4,4-dimethyl-1H—2-benzopyran-1-yl]propyl]piperazine. |
| HN(tetrahydropyridine)-phenyl | 3 | CH₃ | H | 4-fluorophenyl | | 220–223$^a$ | C, 71.06; H, 6.96; N, 2.91; Cl, 6.56; F, 3.52 | 4-phenyl-1-[3-[1-(4-fluorophenyl)-3,4-dihydro-6,7-dimethoxy-4-methyl-1H—2-benzopyran-1-yl]propyl]-1,2,3,6-tetrahydropyridine. |

TABLE I-continued

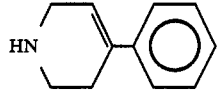

| HNR9R10 | n | R2 | R3 | R8 | °C./Hrs. Misc. | M.P. (°C.) | Anal. (Found) | Name |
|---|---|---|---|---|---|---|---|---|
| 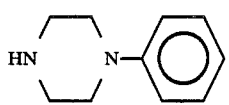 | 3 | CH3 | H | CH3 | | 187–189[b] | C, 69.91; H, 7.55; N, 3.14; Cl, 8.03 | 4-phenyl-1-[3-(3,4-dihydro-6,7-dimethoxy-1,4-dimethyl-1H—2-benzopyran-1-yl) propyl]-1,2,3,6-tetrahydropyridine. |
| 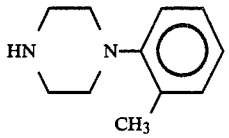 | 3 | CH3 | H | 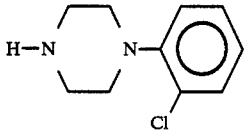 | | 254–256[a] | C, 68.66; H, 7.12; N, 5.09; Cl, 6.76; F, 3.52 | 4-phenyl-1-[3-[1-(4-fluorophenyl)-3,4-dihydro-6,7-dimethoxy-4-methyl-1H—2-benzopyran-1-yl]propyl]-piperazine. |
| 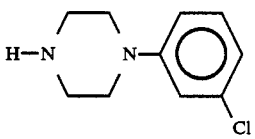 | 3 | CH3 | H | CH3 | | 209–211[a] | C, 67.70; H, 8.26; N, 6.32; Cl, 7.55 | 4-(2-methylphenyl)-1-[3-(3,4-dihydro-6,7-dimethoxy-1,4-dimethyl-1H—2-benzopyran-1-yl)propyl]piperazine. |
| 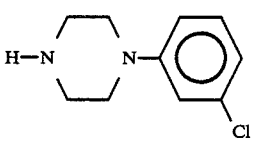 | 2 | CH3 | CH3 | H | | 148–149.5[d] | C, 57.29; H, 6.92; N, 5.61; Cl, 20.48 | 4-(2-chlorophenyl)-1-[2-(3,4-dihydro-6,7-dimethoxy-4,4-dimethyl-1H—2-benzopyran-1-yl)ethyl]piperazine |
| 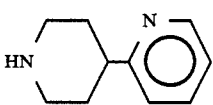 | 2 | CH3 | CH3 | H | | 161–165[a] | C, 61.82; H, 7.09; N, 5.63; Cl, 15.24 | 4-(3-chlorophenyl)-1-[2-(3,4-dihydro-6,7-dimethoxy-4,4-dimethyl-1H—2-benzopyran-1-yl)ethyl]piperazine. |
| 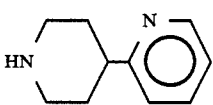 | 2 | CH3 | H | H | | 115.5–117 | C, 66.65; H, 7.30; N, 6.42; Cl, 8.24 | 4-(3-chlorophenyl)-1-[2-(3,4-dihydro-6,7-dimethoxy-4-methyl-1H—2-benzopyran-1-yl)ethyl]piperazine. |
| 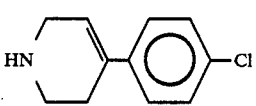 | 3 | H | H | CH3 | | | | 4-(2-pyridyl)-1-[3-(3,4-dihydro-1-methyl-6,7-dimethoxy-1H—2-benzopyran-1-yl)propyl]piperidine. |
| 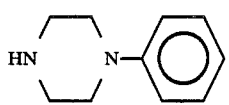 | 2 | CH3 | CH3 | H | | | | 4-(4-chlorophenyl)-1-[2-(3,4-dihydro-6,7-dimethoxy-4,4-dimethyl-1H—2-benzopyran-1-yl)ethyl]-1,2,3,6-tetrahydropyridine. |

TABLE I-continued

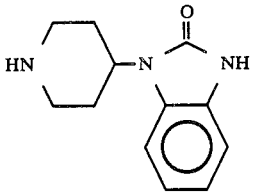

| HNR9R10 | n | R2 | R3 | R8 | °C./Hrs. Misc. | M.P. (°C.) | Anal. (Found) | Name |
|---|---|---|---|---|---|---|---|---|
| (piperidinyl-benzimidazolone structure) | 2 | $CH_3$ | $CH_3$ | H | | | | 1-[2-(3,4-dihydro-6,7-dimethoxy-4,4-dimethyl-1H—2-benzopyran-1-yl)ethyl]-piperidin-4-yl]-1,3-dihydro-2H—benzimidazol-2-one. |

[a] HCl salt
[b] HCl salt hemihydrate
[c] HCl salt hydrate
[d] dihydrochloride salt
[e] dihydrate
[f] trihydrate hydrochloride
[g] dihydrochloride, hemihydrate.

TABLE II (structure: H3CO, H3CO-substituted benzopyran with R4, R5, R8, $(CH_2)_n NR_9R_{10}$)

| HNR9R10 | n | R4 | R5 | R8 | °C./Hrs. Misc. | M.P. (°C.) | Anal. (Found) | Name |
|---|---|---|---|---|---|---|---|---|
| (piperazine with 2-methylphenyl) | 2 | $CH_3$ | $CH_3$ | H | | 222–223[a] | C, 67.77; H, 8.02; N, 6.01 | 4-(2-methylphenyl)-1-[2-(3,4-dihydro-6,7-dimethoxy-3,3-dimethyl-1H—2-benzopyran-1-yl)ethyl]piperazine. |
| (piperazine with 2-methoxyphenyl) | 2 | $CH_3$ | $CH_3$ | H | | 187–189[d] | C, 60.86; H, 7.68; N, 5.51; Cl, 12.76 | 4-(2-methoxyphenyl)-1-[2-(3,4-dihydro-6,7-dimethoxy-3,3-dimethyl-1H—2-benzopyran-1-yl)ethyl]piperazine. |
| (piperazine with 4-fluorophenyl) | 2 | $CH_3$ | $CH_3$ | H | | 161–163[b] | C, 63.20; H, 7.16; N, 6.18 | 4-(4-fluorophenyl)-1-[2-(3,4-dihydro-6,7-dimethoxy-3,3-dimethyl-1H—2-benzopyran-1-yl)ethyl]piperazine. |

[a], [b] and [d] are as defined for Table I.

I claim:
1. A compound selected from the group consisting of
4-phenyl-1-[2-(3,4-dihydro-6,7-dimethoxy-4-methyl-1H-2-benzopyran-1-yl)ethyl]piperazine;
4-phenyl-1-[2-(3,4-dihydro-6,7-dimethoxy-4-methyl-1H-2-benzopyran-1-yl)ethyl]piperazine, dihydrochloride;
4-(3-chlorophenyl)-1-[2-(3,4-dihydro-6,7-dimethoxy-4-methyl-1H-2-benzopyran-1-yl)ethyl]piperazine;
4-(2-chlorophenyl)-1-[2-(3,4-dihydro-6,7-dimethoxy-4-methyl-1H-2-benzopyran-1-yl)ethyl]piperazine;
4-(2-chlorophenyl)-1-[2-(3,4-dihydro-6,7-dimethoxy-4-methyl-1H-2-benzopyran-1-yl)ethyl]piperazine, dihydrochloride;
4-phenyl-1-[3-[1-(4-fluorophenyl)-3,4-dihydro-6,7-dimethoxy-4-methyl-1H-2-benzopyran-1-yl]propyl]piperazine; and
4-phenyl-1-[3-[1-(4-fluorophenyl)-3,4-dihydro-6,7-dimethoxy-4-methyl-1H-2-benzopyran-1-yl]propyl]piperazine, monohydrochloride.

2. A compound selected from the group consisting of
1-(4-chlorophenyl)-4-[2-(3,4-dihydro-6,7-dimethoxy-4,4-dimethyl-1H-2-benzopyran-1-yl)ethyl]piperazine;
1-(4-chlorophenyl)-4-[2-(3,4-dihydro-6,7-dimethoxy-4,4-dimethyl-1H-2-benzopyran-1-yl)ethyl]piperazine, monohydrochloride;
1-[2-(3,4-dihydro-6,7-dimethoxy-4,4-dimethyl-1H-2-benzopyran-1-yl)ethyl]-4-(4-methoxyphenyl)piperazine;

1-[2-(3,4-dihydro-6,7-dimethoxy-4,4-dimethyl-1H-2-benzopyran-1-yl)ethyl]-4-(4-methoxyphenyl)piperazine, dihydrochloride;

1-[2-(3,4-dihydro-6,7-dimethoxy-4,4-dimethyl-1H-2-benzopyran-1-yl)ethyl]-4-(2-pyridyl)piperazine;

1-[2-(3,4-dihydro-6,7-dimethoxy-4,4-dimethyl-1H-2-benzopyran-1-yl)ethyl]-4-(2-pyridyl)piperazine, dihydrochloride;

1-[2-(3,4-dihydro-6,7-dimethoxy-4,4-dimethyl-1H-2-benzopyran-1-yl)ethyl]4-(4-fluorophenyl)piperazine;

1-[2-(3,4-dihydro-6,7-dimethoxy-4,4-dimethyl-1H-benzopyran-1-yl)ethyl]4-(4-fluorophenyl)piperazine, hydrochloride;

4-phenyl-1-[2-(3,4-dihydro-4,4-dimethyl-6,7-dimethoxy-1H-2-benzopyran-1-yl)ethyl]piperazine;

4-phenyl-1-[2-(3,4-dihydro-4,4-dimethyl-6,7-dimethoxy-1H-2-benzopyran-1-yl)ethyl]piperazine, hydrate;

4-(2-chlorophenyl)-1-[2-(3,4-dihydro-6,7-dimethoxy-4,4-dimethyl-1H-2-benzopyran-1-yl)ethyl]piperazine;

4-(2-chlorophenyl)-1-[2-(3,4-dihydro-6,7-dimethoxy-4,4-dimethyl-1H-2-benzopyran-1-yl)ethyl]piperazine, dihydrochloride;

4-(3-chlorophenyl)-1-[2-(3,4-dihydro-6,7-dimethoxy-4,4-dimethyl-1H-2-benzopyran-1-yl)ethyl]piperazine;

4-(3-chlorophenyl)-1-[2-(3,4-dihydro-6,7-dimethoxy-4,4-dimethyl-1H-2-benzopyran-1-yl)ethyl]piperazine, monohydrochloride;

4-phenyl-1-[3-(3,4-dihydro-6,7-dimethoxy-1,4,4-trimethyl-1H-2-benzopyran-1-yl)propyl]piperazine;

4-phenyl-1-[3-(3,4-dihydro-6,7-dimethoxy-1,4,4-trimethyl-1H-2-benzopyran-1-yl)propyl]piperazine, dihydrochloride;

4,(4-fluorophenyl)-1-[3(3,4-dihydro-6,7-dimethoxy-1,4,4-trimethyl-1H-2-benzopyran-1-yl)propyl-piperazine;

4-(4-fluorophenyl)-1-[3-(3,4-dihydro-6,7-dimethoxy-1,4,4-trimethyl-1H-2-benzopyran-1-yl)propyl]piperazine, dihydrochloride, hemihydrate;

4-phenyl-1-[3-[1-(4-fluorophenyl)-3,4-dihydro-6,7-dimethoxy-4,4-dimethyl-1H-2-benzopyran-1-yl]propyl]piperazine;

4-phenyl-1-[3-[1-(4-fluorophenyl)-3,4-dihydro-6,7-dimethoxy-4,4-dimethyl-1H-2-benzopyran-1-yl]propyl]piperazine, monohydrochloride, monohydrate;

4-(2-methoxyphenyl)-1-[2-(3,4-dihydro-6,7-dimethoxy-3,3-dimethyl-1H-2-benzopyran-1-yl)ethyl]piperazine;

4-(2-methoxyphenyl)-1-[2-(3,4-dihydro-6,7-dimethoxy-3,3-dimethyl-1H-2-benzopyran-1-yl)ethyl]piperazine, dihydrochloride;

4-(4-fluorophenyl)-1-[2-(3,4-dihydro-6,7-dimethoxy-3,3-dimethyl-1H-2-benzopyran-1-yl)ethyl]piperazine;

4-(4-fluorophenyl)-1-[2-(3,4-dihydro-6,7-dimethoxy-3,3-dimethyl-1H-2-benzopyran-1-yl)ethyl]piperazine, monohydrochloride, hemihydrate.

* * * * *